United States Patent
Hue et al.

(10) Patent No.: US 10,724,095 B2
(45) Date of Patent: Jul. 28, 2020

(54) DIAGNOSTIC MARKERS OF IMMUNOSENESCENCE AND METHODS FOR DETERMINING THE SUSCEPTIBILITY TO NOSOCOMIAL INFECTIONS

(71) Applicants: INSERM (INSTITUT NATIONAL DE LA SANTÉ ET DE LA RECHERCHE MÉDICALE), Paris (FR); ASSISTANCE PUBLIQUE-HÔPITAUX DE PARIS (APHP), Paris (FR); UNIVERSITÉ PARIS-EST CRÉTEIL VAL DE MARNE, Creteil (FR)

(72) Inventors: Sophie Hue, Créteil (FR); Yves Levy, Créteil (FR)

(73) Assignees: INSERM (INSTITUT NATIONAL DE LA SANTÉ ET DE LA RECHERCHE MÉDICALE), Paris (FR); ASSISTANCE PUBLIQUE-HÔPITAUX DE PARIS (APHP), Paris (FR); UNIVERSITÉ PARIS-EST CRÉTEIL VAL DE MARNE, Creteil (FR)

( * ) Notice: Subject to any disclaimer, the term of this patent is extended or adjusted under 35 U.S.C. 154(b) by 49 days.

(21) Appl. No.: 16/060,775

(22) PCT Filed: Dec. 15, 2016

(86) PCT No.: PCT/EP2016/081283
§ 371 (c)(1),
(2) Date: Jun. 8, 2018

(87) PCT Pub. No.: WO2017/103001
PCT Pub. Date: Jun. 22, 2017

(65) Prior Publication Data
US 2019/0010546 A1    Jan. 10, 2019

(30) Foreign Application Priority Data
Dec. 16, 2015 (EP) .................................... 15307024

(51) Int. Cl.
G01N 33/53 (2006.01)
C12Q 1/6876 (2018.01)
G01N 33/68 (2006.01)

(52) U.S. Cl.
CPC ....... *C12Q 1/6876* (2013.01); *G01N 33/6893* (2013.01); *C12Q 2600/106* (2013.01); *G01N 2333/4737* (2013.01); *G01N 2333/5412* (2013.01); *G01N 2333/70596* (2013.01); *G01N 2800/24* (2013.01); *G01N 2800/26* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 5,292,636 A * | 3/1994 | Kung ................. C07K 16/2812 435/34 |
| 5,545,566 A * | 8/1996 | Growden ............... G01N 33/92 436/71 |
| 2015/0140036 A1* | 5/2015 | Mannick .............. A61K 39/092 424/209.1 |

FOREIGN PATENT DOCUMENTS

WO    2015/054039 A1    4/2015
WO    2015/143367 A2    9/2015

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Franceschi et al., Inflamm-aging An Evolutionary Perspective on Immunosenescence, Annals of New York Academy of Sciences 908, 2000, pp. 244-254. (Year: 2000).*
Stahl et al., Cell Therapy Strategies to Combat Immunosenescence, Organogenesis 11, Nov. 2015, pp. 159-172. (Year: 2015).*
N. G. Sandler et al: "Plasma Levels of Soluble CD14 Independently Predict Mortality in HIV Infection", Journal of Infectious Diseases. JID, vol. 203, No. 6, Jan. 20, 2011, pp. 780-790.
P. W. Hunt et al: "Gut Epithelial Barrier Dysfunction and Innate Immune Activation Predict Mortality in Treated HIV Infection", Journal of Infectious Diseases. JID, vol. 210, No. 8, Apr. 21, 2014, pp. 1228-1238.
Otto O. Yang et al: "Immunomodulation of Antiretroviral Drug-Suppressed Chronic HIV-1 Infection in an Oral Probiotic Double-Blind Placebo-Controlled Trial", AIDS Research and Human Retroviruses., vol. 30, No. 10, Aug. 15, 2014, pp. 988-995.
Amanda K. Steele et al: "Contribution of Intestinal Barrier Damage, Microbial Translocation and HIV-1 Infection Status to an Inflammaging Signature", PLOS ONE, vol. 9, No. 5, May 12, 2014, p. e97171.
O Goovaerts et al: "TB-IRIS is marked by acute phase response related elevation of LBP and IL-6", Immunology, vol. 137, No. s1, Sep. 5, 2012, p. 522, 2016.

(Continued)

*Primary Examiner* — Gary Counts
(74) *Attorney, Agent, or Firm* — W&C IP

(57) ABSTRACT

The invention provides diagnostic markers of immunosenescence and methods of identifying individuals with impaired immune function based on the expression level of a combination of such markers in a biological sample obtained from said individual. Such combination of markers is useful for determining the susceptibility to nosocomial infections of an individual. Such combination of markers is also useful for predicting whether an individual will respond to active vaccination and become protected against recurring diseases.

9 Claims, No Drawings

(56) References Cited

OTHER PUBLICATIONS

Kv Shmagel et al: "Systemic inflammation and liver damage in HIV/hepatitis C virus coinfection", HIV Medicine, vol. 17, No. 8, May 17, 216, pp. 581-589.

Mohammad-Ali Jenabian et al: Influence oh Hepatitis C Virus Sustained Virological Response on Immunosuppressive Tryptophan Catabolism in ART-Treated HIV/HCV Coinfected Patients, Mar. 1, 2016, p. 258.

Odin Goovaerts et al: "LPS-Binding Protein and IL-6 Mark Paradoxical Tuberculosis Immune Reconstitution Inflammatory Syndrome in HIV Patients", PLOS ONE, vol. 8, No. 11, Nov. 28, 2013, p. e81856.

Joanna R. Santos-Oliveira et al: "Microbial Translocation Induces an Intense Proinflammatory Response in Patients With Visceral Leishmaniasis and HIV Type 1 Coinfection", Journal of Infectious Diseases. JID., vol. 208, No. 1, Mar. 28, 2013, pp. 57-66.

Joanna R. Santos-Oliveira et al: "Evidence That Lipopolisaccharide May Contribute to the Cytokine Storm and Cellular Activation in Patients with Visceral Leishmaniasis", PLOS Negleted Tropical Diseases, vol. 5, No. 7, Jul. 12, 2011, p. e1198.

Stephen Kovacs et al: "Evidence of T cell lymphopenia in the colonic mucosa in idiopathic CD4 lymphocytopenia patients (HEM4P. 250)" The Journal of Immunology, Journal of Immunology, May 1, 2014, p. 117.1.

Maconcepcion Romero-Sanchez et al: "Different biological significance of sCD14 and LPS in HIV-infection: Importance of the immunovirology stage and association with HIV-diseases progression markers", Journal of Infection., vol. 65, No. 5, Jun. 20, 2012, pp. 431-438.

* cited by examiner

DIAGNOSTIC MARKERS OF IMMUNOSENESCENCE AND METHODS FOR DETERMINING THE SUSCEPTIBILITY TO NOSOCOMIAL INFECTIONS

FIELD OF THE INVENTION

The invention relates to the field of medicine, and more particularly to markers of immunosenescence and methods for determining the susceptibility to nosocomial infections.

BACKGROUND OF THE INVENTION

Healthcare-associated infections (HAI) constitute a major public health concern as they are common and associated with both high morbidity and mortality rates and high healthcare costs[1,2]. 54% of all HAI occurred in people aged 65 or over[3]. Risk factors for HAI vary with the infection site, healthcare setting, and patient age. We previously reported that among patients aged 70 years or over, invasive procedures and comorbidities assessed using the Cumulative Illness Rating Scale for Geriatrics (CIRS-G), were strong risk factors for HAI[4]. In elderly individuals, the increased susceptibility to severe infections and decreased efficacy of vaccination may reflect ageing of the immune system, called immunosenescence, which involves nearly all the components of the immune system[5,6].

Two main lines of hypothesis are currently debated to explain immunosenescence. On the one hand, a major role has been ascribed to the progressive decline in naive circulating T-cell counts (paralleling the involution of the thymus), expansion of memory T-cells, and accumulation of terminally differentiated effector CD8 T-cells[7]. Cytomegalovirus (CMV) is also considered crucial among the repeated antigenic stimuli responsible for the accumulation of oligoclonal effector CD8 T cells[8]. The Immune Risk Phenotype (IRP) coined by Pawelec et al[9] takes into account these alterations. It includes inversion of CD4/CD8 ratio, and expansion of CD28 negative CD8 T-cells, associated with positive CMV serology[10]. In a previous study, at baseline, patients with subsequent HAI indeed showed lower naive $CD4^+$ and $CD8^+$ T cell counts, and higher counts of $CD28^-$ $CD8^+$ T cells[11]. However, parameters alterations remained within normal range. IRP measurement showed that patients exhibiting the IRP had a higher rate of nosocomial infection, although only in the lung.

On the other hand, low-grade chronic inflammation is often encountered in elderly people[12]. The mechanisms that underlie this ageing-associated heightened level of basal inflammation might involve changes in numbers and functions of innate immune cells, leading to inefficient response as well as decreased tolerance. Chronic inflammation is commonly encountered in atherosclerosis[13], Alzheimer's disease[14], and HIV infection[15]. Microbial translocation has recently been suggested to have a key role in driving this persistent immune activation in individuals with chronic HIV infection[16]. Microbial translocation consists in (i) the translocation of commensal microbial products from the intestinal lumen, which is now known to occur in healthy conditions; and (ii) transfer into the systemic circulation (in the absence of overt bacteraemia), which is abnormal and is accompanied by a persistent immune activation leading to low grade systemic inflammatory response[17].

Recent evidence suggests that disruption of the intestinal barrier is associated with aging[18]. The first event leading to microbial translocation consists in the alteration of the epithelial barrier, monitored using plasma intestinal-type fatty acid-binding protein (I-FABP) concentration, which reflects apoptosis of the epithelial cell layer[19]. Microbial products are physiologically controlled by the gut immune system and do not reach periphery. When the gut immune system cannot complete its firewall function, microbial translocation occurs. Once in the circulation, microbial products can stimulate innate cells such as monocytes and macrophages. Endotoxin (lipopolysaccharide, LPS), a component present at the membrane of Gram-negative bacteria binds to several different extracellular and cell surface proteins—the LPS-binding protein (LBP), CD14, MD-2, and Toll-like receptor (TLR)-4. After LPS stimulation, activation of monocytes/macrophages leads to the shedding of surface CD14. soluble CD14 (sCD14) released into blood is elevated in patients with infection and is reported to increase in severity dependent manner[20,21].

Determining a patient's susceptibility to nosocomial infections is therefore essential in order to be able to offer personalized management and to endeavour to minimise additional risks of a fatal outcome. There is therefore a true need for other immunological markers with which it is possible to obtain easy, fast prediction of a patient's susceptibility to nosocomial infections. The ability to identify persons the most at risk of contracting a nosocomial infection would allow the setting up of better adapted and better targeted preventive therapy.

Moreover, deterioration of immune function is a prominent hallmark of aging and is only partially explainable by a loss of naïve and central memory CD4 T cells due to thymic involution. Defects in both the innate and adaptive immune system of the elderly have been described and include changes in immune cell-subsets abundance and relative frequencies, altered haematopoiesis, impairments in antigen presentation, decreased B cell as well as T cell proliferation, a reduced TCR repertoire and defect in antibody production (Weiskopf et al., 2009). Ultimately these alterations result in a sharp decline in the response to new and persisting antigens also called as immunosenescence as previously mentioned.

Thus it is not surprising that infectious diseases are one of the major causes of mortality in those over the age of 65 and that protective vaccination of the elderly is more difficult to establish than in younger individuals (Goodwin, 2006).

Due to the complexity of the immune system, studies of immunosenescence often only investigate one or a few variables of an individual's immune system. This has made it difficult to draw general conclusions about the phenomena being described or how they might relate to each other. Individuals who suffer from an impaired immune function generally face the risk of increased morbidity and mortality. This is particularly relevant for older individuals who show a reduced response to vaccination (Strindhall et al., 2007).

Active immunization and activation of T cell-mediated as well as humoral immune response can be achieved through the administration of immunogenic material or vaccines. Vaccination seeks to prevent, ameliorate or even treat against the harmful effects of pathogens and carcinogens, and regular vaccination has become an integral part of preventive medicine. Unfortunately, following vaccination, older individuals often don't develop a fully functioning adaptive immune response, as would be evidenced by a strong antibody production against an introduced immunogen, and, thus, do not obtain the benefits of long-lasting protection against recurring diseases.

Accordingly, one of the most challenging topics facing the maintenance of good health and longevity is the identification of immunocompromised individuals who might appear healthy, but who have an underlying, undetected impairment of immune function and, so, face the risk of increased morbidity and mortality. Additionally, predicting with a very high accuracy whether an individual will respond appropriately to active vaccination and become protected against recurring diseases is a primordial issue for developing personalized treatment plans and optimal immunizations schedules for these patients.

SUMMARY OF THE INVENTION

In a first aspect, the invention relates to an in vitro method for determining the patient's susceptibility to healthcare-associated infections (HAI), comprising a step of determining the expression level of C-reactive protein (CRP) and/or interleukin-6 (IL-6), intestinal-type fatty acid-binding protein (I-FABP) and at least one monocyte activation marker selected from the group consisting of soluble CD14 (sCD14) and soluble CD163 (sCD163) in a biological sample obtained from said patient.

In a second aspect, the invention relates to an in vitro method for diagnosing impaired immune function or immunosenescence in a subject, comprising a step of determining the expression level of CRP and/or IL-6, I-FABP and at least one monocyte activation marker selected from the group consisting of sCD14 and sCD163 in a biological sample obtained from said subject.

In a third aspect, the invention relates to an in vitro method for predicting the responsiveness of a subject to active vaccination, comprising a step of determining the expression level of CRP and/or IL-6, I-FABP and at least one monocyte activation marker selected from the group consisting of sCD14 and sCD163 in a biological sample obtained from said subject.

In a fourth aspect, the invention relates to a method for adjusting the anti-infective treatment administered to a patient susceptible to HAI, comprising the steps of: (i) performing the method for determining the patient's susceptibility to HAI according to the invention, and (ii) adjusting the anti-infective treatment.

In a fifth aspect, the invention relates to a method for adjusting the vaccination regime and/or dosing administered to a subject, comprising the steps of: (i) performing the method predicting the responsiveness of a subject to vaccination according to the invention, and (ii) adjusting the vaccination regime and/or dosing.

In a sixth aspect, the invention relates to a kit comprising the means for determining the expression levels of CRP and/or IL-6, I-FABP and at least one monocyte activation marker selected from the group consisting of soluble sCD14 and sCD163.

DETAILED DESCRIPTION OF THE INVENTION

The inventors hypothesized that low-grade inflammation could be driven by microbial translocation and could be associated with high risk to develop HAI. Gut epithelium, altered by age, might not remain as tight as to prevent increased translocation of microbial products, and association with altered local innate immune responses could lead to bona fide microbial translocation. Accordingly, they measured serum hs-CRP (High-sensitivity-C-reactive protein) and IL-6 (interleukin-6), as a marker of low grade inflammation in association with serum I-FABP as a marker of epithelial cells apoptosis and integrity of epithelial barrier, and serum sCD14, as a marker of activation of the monocyte-macrophage compartment by translocated microbial products. These markers were measured at admission in older patients hospitalized in the geriatric rehabilitation unit.

The inventors showed that increased levels of hs-CRP and/or IL-6, I-FABP and sCD14 constitute a profile that allows identifying patients at high risk of developing HAI. The inventors indeed found hs-CRP elevation (≥6.02 mg/L) was associated with a significantly higher HAI risk when the I-FABP level was in the highest quartile (OR, 4; 95% CI, 1.39-11.49; P=0.010). The patients with high levels of all three markers (hs-CRP, I-FABP and sCD14) had an 11-fold higher risk of HAI (OR, 10.8; 95% CI, 2.28-51.1; P=0.003). In contrast, combined hs-CRP and I-FABP elevation without sCD14 elevation was not associated with a significantly higher HAI risk.

The inventors substituted IL-6 for hs-CRP as the marker for low-grade inflammation, the results were unchanged, IL-6 elevation (≥4.99 pg/L) was associated with a significantly higher HAI risk when the I-FABP level was in the highest quartile, and patients with high levels of all three markers had a 6-fold higher HAI risk.

Definitions

Throughout the specification, several terms are employed and are defined in the following paragraphs.

As used herein, the term "C-reactive protein (CRP) gene" encodes a protein of 224 amino acids which is a member of the pentraxin family of proteins. CRP is an annular (ring-shaped), pentameric protein found in blood plasma, whose levels rise in response to inflammation. The term includes naturally occurring CRP and variants thereof. The naturally occurring human CRP protein has an aminoacid sequence as shown in the GenBank Protein Accession under No. NP_000558 and is encoded by the nucleic acid sequence provided in the GenBank database under Accession No. NM_000567.

As used herein, the terms "IL-6 gene" or "interleukin-6 gene" (NCBI Gene ID: 3569) encodes a protein of 212 amino acids, interleukin-6 (IL-6) (Uniprot reference: P05231). IL-6 is a cytokine which functions in inflammation and the maturation of B cells. In addition, the encoded protein has been shown to be an endogenous pyrogen capable of inducing fever in people with autoimmune diseases or infections.

As used herein, the term "intestinal-type fatty acid-binding protein (I-FABP) gene" encodes a protein of 132 amino acids also known as Fatty acid-binding protein 2 (FABP2). The term includes naturally occurring I-FABP and variants thereof. The naturally occurring human I-FABP protein has an aminoacid sequence as shown in the GenBank Protein Accession under No. NP_000125 and is encoded by the nucleic acid sequence provided in the GenBank database under Accession No. NM_000134.

As used herein, the term "Cluster of Differentiation (CD14) gene" encodes a glycoprotein of 375 amino acids which has been identified as a differentiation maker expressed on the monocyte membrane, and it is known to have the function of a receptor for LPS (lipopolysaccharide). Known molecular species of the CD14 molecule include two types, namely, membrane-bound CD14 (mCD14) which is expressed on the cell surface and soluble CD14 (sCD14). The term includes naturally occurring CD14 and variants thereof. The naturally occurring human CD14 protein has an aminoacid sequence as shown in the GenBank Protein under Accession No. NP_000582 and is encoded by the nucleic acid sequence provided in the GenBank database under Accession No. NM_000591. Known sCD14 molecular species include the one having a molecular weight of about 55 kDa and the one having a molecular weight of about 49 kDa and these are believed to be produced by secretion from liver as well as cleavage by mCD14 enzyme associated by the activation of a monocyte.

As used herein, the term "Cluster of Differentiation (CD163) gene" encodes a protein of 1156 amino acids which has been identified as a scavenger receptor for the hemoglobin-haptoglobin complex and it is known to mark cells of monocyte/macrophage lineage. Known molecular species of the CD163 molecule include two types, namely, membrane-bound CD163 (mCD163) which is expressed on the cell surface and soluble CD163 (sCD163). The term includes naturally occurring CD163 and variants thereof. The naturally occurring human CD163 protein has an aminoacid sequence as shown in the GenBank Protein under Accession No. NP_004235.4 and is encoded by the nucleic acid sequence provided in the GenBank database under Accession No. NM_004244. Known sCD163 molecular species include the one generated by ectodomain shedding of the membrane bound receptor. sCD163 is upregulated in a large range of inflammatory diseases.

As used herein, the term "gene" refers to a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, "determining" encompasses detecting or quantifying. Indeed, an expression level can be qualitative or quantitative. Thus, a determination of whether a polynucleotide or polypeptide is present or absent (e.g., detectable or undetectable) constitutes determining its expression level in various embodiments while in other embodiments, a quantitative level is determined. A single measurement can provide information about the level of expression, activity, or both. Thus, evaluating the expression level of a protein includes evaluating one or more parameters or features that provide information about the level of expression of the protein, the activity of the protein, or both.

As used herein, "detecting" means determining if CRP, I-FABP, sCD14 and/or sCD163 is present or not in a biological sample and "quantifying" means determining the amount of CRP, I-FABP, sCD14 and/or sCD163 in a biological sample.

As used herein, the term "predetermined reference level" refers to the expression levels of CRP, I-FABP, sCD14 and/or sCD163 in biological samples obtained from the general population or from a selected population of subjects. For example, the selected population may be comprised of apparently healthy patient, such as individuals who have not previously had any sign or symptoms indicating the presence of infections. A "predetermined reference level" may be determined, for example, by determining the expression level of CRP, I-FABP, sCD14 and/or sCD163 nucleic acids or encoded polypeptides, in a corresponding biological sample obtained from one or more control subject(s) (e.g., not suffering from nosocomial infection or known not to be susceptible to such a disease). When such a predetermined reference level is used, a higher or increased levels determined in a biological sample (i.e. a test sample obtained from the subject) is indicative for example that said patient is at risk of developing nosocomial infections. The predetermined reference level may be established based upon measurements of the expression levels of the biomarkers of interest in a blood sample obtained from a large general population cohort.

As used herein, the term "biological sample" refers to a biological sample obtained for the purpose of in vitro evaluation. In the methods of the invention, the biological sample may comprise any body fluid obtained from a patient. Typical biological samples to be used in the methods according to the invention are blood samples (e.g. whole blood sample, serum sample, or plasma sample). A biological sample can be optionally pre-treated or processed prior to be used. Examples of pre-treatment steps include the addition of a reagent such as a stabilizer, a preservative, a fixant, a lysing reagent, a diluent, an anti-apoptotic reagent, a buffering reagent, an osmolarity regulating reagent, a pH regulating reagent, etc . . . .

Prognostic and Diagnostic Methods of the Invention

In a first aspect, the invention relates to an in vitro method for determining the patient's susceptibility to healthcare-associated infections, comprising a step of determining the expression level of High-sensitivity-C-reactive protein (hs-CRP), intestinal-type fatty acid-binding protein (I-FABP) and at least one monocyte activation marker selected from the group consisting of soluble CD14 (sCD14) and soluble CD163 (sCD163) in a biological sample obtained from said patient.

In a further aspect, the invention relates to an in vitro method for determining the patient's susceptibility to healthcare-associated infections, comprising a step of determining the expression level of C-reactive protein (hs_CRP) and/or interleukin-6 (IL-6), intestinal-type fatty acid-binding protein (I-FABP) and at least one monocyte activation marker selected from the group consisting of soluble CD14 (sCD14) and soluble CD163 (sCD163) in a biological sample obtained from said patient.

The terms "nosocomial infection", "healthcare-associated infection" (HAI) and "hospital-acquired infection" are used interchangeably. By "nosocomial infection" is meant any infection, chiefly bacterial but also viral and fungal, which occurs in a healthcare facility during or after patient management (diagnosis, therapeutic, palliative, preventive or rehabilitation therapy), and which was neither present nor under incubation at the time patient management was initiated. When the infectious state is not specifically known at the start of patient management, a time of at least 48 hours or a time longer than the incubation period is generally accepted to define a nosocomial infection.

In one embodiment of the invention, the nosocomial infection is a nosocomial bacterial infection.

As used herein, the terms "patient" encompasses human beings who have reduced or deteriorated immune defences subsequent to pathologies directly damaging their immunologic competence, or due to their general condition. These patients, in particular those the upper age range (the elderly) and those in intensive care units than in other hospital units are especially sensitive to infections in general and in particular to the onset of nosocomial infections. The high incidence of nosocomial infections in this sector can be accounted for by the harmful combination of several endogenous risk factors: patient exposure to invasive procedures (artificial ventilation, urinary and other catheterization), the seriousness of patient condition (and associated co-morbidities) and treatments (multiple transfusions, sedation). Nevertheless, despite all the hygiene and monitoring measures taken (exogenous risks) and the consideration given to these endogenous risk factors, the incidence of nosocomial infections remains stable or is only slightly on the decrease.

In one embodiment of the invention, the patient is an elderly individual.

The terms "elderly individual", "elderly" or "older individual", as used herein, define a human being who is about 60 years of age or older.

In another embodiment of the invention, the patient is a patient affected with any condition leading to immunodeficiency (immunosuppressive therapy, primary or secondary immunodeficiency or a patient diagnosed with co-morbidity factors (such as chronic heart and pulmonary, metabolic and neurodegenerative diseases). In a particular embodiment of the invention, the patient is an HIV-infected patient or infected by another virus such as a CMV-infected patient. In another particular embodiment of the invention, the patient is a patient hospitalized in intensive care and/or having sustained an insult (surgery, burns, trauma . . . ). In still another particular embodiment of the invention, the patient is a patient with a chronic disease such as diabetes including diabetes mellitus or a thymectomized patient.

In a particular embodiment of the invention, the biological sample is a blood sample (e.g. whole blood sample, serum sample, or plasma sample).

In one embodiment, the invention relates to an in vitro method for determining the patient's susceptibility to nosocomial infections, comprising a step of determining the expression level of hs-CRP, I-FABP and sCD14 in a biological sample obtained from said patient.

In another embodiment, the invention relates to an in vitro method for determining the patient's susceptibility to nosocomial infections, comprising a step of determining the expression level of IL-6, I-FABP and sCD14 in a biological sample obtained from said patient.

In another embodiment, the invention relates to an in vitro method for determining the patient's susceptibility to nosocomial infections, comprising a step of determining the expression level of hs-CRP, I-FABP and sCD163 in a biological sample obtained from said patient.

In another embodiment, the invention relates to an in vitro method for determining the patient's susceptibility to nosocomial infections, comprising a step of determining the expression level of IL-6, I-FABP and sCD163 in a biological sample obtained from said patient.

In another embodiment, the invention relates to an in vitro method for determining the patient's susceptibility to nosocomial infections, comprising a step of determining the expression level of hs-CRP, I-FABP, sCD14 and sCD163 in a biological sample obtained from said patient.

In another embodiment, the invention relates to an in vitro method for determining the patient's susceptibility to nosocomial infections, comprising a step of determining the expression level of IL-6, I-FABP, sCD14 and sCD163 in a biological sample obtained from said patient.

In another embodiment, the invention relates to an in vitro method for determining the patient's susceptibility to nosocomial infections, comprising a step of determining the expression level of hs-CRP, IL-6, I-FABP and sCD14 in a biological sample obtained from said patient.

In another embodiment, the invention relates to an in vitro method for determining the patient's susceptibility to nosocomial infections, comprising a step of determining the expression level of hs-CRP, IL-6, I-FABP and sCD163 in a biological sample obtained from said patient.

In another embodiment, the invention relates to an in vitro method for determining the patient's susceptibility to nosocomial infections, comprising a step of determining the expression level of hs-CRP, IL-6, I-FABP, sCD14 and sCD163 in a biological sample obtained from said patient.

In one embodiment, said method comprises a step of (i) determining the expression level of the hs-CRP, I-FABP and at least one monocyte activation marker selected from the group consisting of sCD14 and sCD163 in a biological sample obtained from said patient, and (ii) comparing said expression levels with their predetermined reference levels, wherein an increase in the expression levels of the hs-CRP, I-FABP and at least one monocyte activation marker selected from the group consisting of sCD14 and sCD163 is indicative of being susceptible (or at risk) of healthcare-associated infections.

In one embodiment, said method comprises a step of (i) determining the expression level of the hs-CRP and/or IL-6, I-FABP and at least one monocyte activation marker selected from the group consisting of sCD14 and sCD163 in a biological sample obtained from said patient, and (ii) comparing said expression levels with their predetermined reference levels, wherein an increase in the expression levels of the hs-CRP and/or IL-6, I-FABP and at least one monocyte activation marker selected from the group consisting of sCD14 and sCD163 is indicative of being susceptible (or at risk) of healthcare-associated infections.

In one embodiment, said method comprises a step of (i) determining the expression level of the hs-CRP, I-FABP and sCD14 in a biological sample obtained from said patient, and (ii) comparing said expression levels with their predetermined reference levels, wherein an increase in the expression levels of the hs-CRP, I-FABP and sCD14 is indicative of being susceptible (or at risk) of healthcare-associated infections.

In one embodiment, said method comprises a step of (i) determining the expression level of the IL-6, I-FABP and sCD14 in a biological sample obtained from said patient, and (ii) comparing said expression levels with their predetermined reference levels, wherein an increase in the expression levels of the IL-6, I-FABP and sCD14 is indicative of being susceptible (or at risk) of healthcare-associated infections.

In a preferred embodiment of the invention, the predetermined reference serum hs-CRP level is approximately 6.0 mg/L. In one embodiment of the invention, the predetermined reference serum I-FABP level is approximately 2000 pg/mL. In one embodiment of the invention, the predetermined reference serum sCD14 level is approximately 0.7 μg/mL. In one embodiment of the invention, the predetermined reference serum IL-6 level is approximately 5.0 pg/L.

In one embodiment, said method comprises a step of (i) determining the expression level of the hs-CRP, I-FABP and sCD163 in a biological sample obtained from said patient, and (ii) comparing said expression levels with their predetermined reference levels, wherein an increase in the expression levels of the hs-CRP, I-FABP and sCD163 is indicative of being susceptible (or at risk) of healthcare-associated infections.

In one embodiment, said method comprises a step of (i) determining the expression level of the IL-6, I-FABP and sCD163 in a biological sample obtained from said patient, and (ii) comparing said expression levels with their predetermined reference levels, wherein an increase in the expression levels of the IL-6, I-FABP and sCD163 is indicative of being susceptible (or at risk) of healthcare-associated infections.

In one embodiment, said method comprises a step of (i) determining the expression level of the hs-CRP, I-FABP, sCD14 and sCD163 in a biological sample obtained from said patient, and (ii) comparing said expression levels with their predetermined reference levels, wherein an increase in the expression levels of the hs-CRP, I-FABP, sCD14 and sCD163 is indicative of being susceptible (or at risk) of healthcare-associated infections.

In one embodiment, said method comprises a step of (i) determining the expression level of the IL-6, I-FABP, sCD14 and sCD163 in a biological sample obtained from said patient, and (ii) comparing said expression levels with their predetermined reference levels, wherein an increase in the expression levels of the IL-6, I-FABP, sCD14 and sCD163 is indicative of being susceptible (or at risk) of healthcare-associated infections.

In one embodiment, said method comprises a step of (i) determining the expression level of the hs-CRP, IL-6, I-FABP and sCD14 in a biological sample obtained from said patient, and (ii) comparing said expression levels with their predetermined reference levels, wherein an increase in the expression levels of the hs-CRP, IL-6, I-FABP and sCD14 is indicative of being susceptible (or at risk) of healthcare-associated infections.

In one embodiment, said method comprises a step of (i) determining the expression level of the hs-CRP, IL-6, I-FABP and sCD163 in a biological sample obtained from said patient, and (ii) comparing said expression levels with their predetermined reference levels, wherein an increase in the expression levels of the hs-CRP, IL-6, I-FABP and sCD163 is indicative of being susceptible (or at risk) of healthcare-associated infections.

In one embodiment, said method comprises a step of (i) determining the expression level of the hs-CRP, IL-6, I-FABP, sCD14 and sCD163 in a biological sample obtained from said patient, and (ii) comparing said expression levels with their predetermined reference levels, wherein an increase in the expression levels of the hs-CRP, IL-6, I-FABP sCD14 and sCD163 is indicative of being susceptible (or at risk) of healthcare-associated infections.

In a second aspect, the invention relates to an in vitro method for diagnosing impaired immune function or immunosenescence in a subject, comprising a step of determining the expression level of hs-CRP, I-FABP and at least one monocyte activation marker selected from the group consisting of sCD14 and sCD163 in a biological sample obtained from said subject.

In a further aspect, the invention relates to an in vitro method for diagnosing impaired immune function or immunosenescence in a subject, comprising a step of determining the expression level of hsCRP and/or IL-6, I-FABP and at least one monocyte activation marker selected from the group consisting of sCD14 and sCD163 in a biological sample obtained from said subject.

The term "impaired immune function", as used herein, refers to any reduction in immune function in an individual, as compared to a fully healthy individual. Individuals with an impaired immune function are readily identifiable by substantially increased abundance of $CD8^+$ $CD28^-$ cells or more broadly by reduced cytokine responses, increased baseline phosphoprotein levels and other co-occurring measures.

As used herein, the term "immunosenescence" refers to the defects in both the innate and adaptive immune system have been described and include changes in immune cell subsets abundance and relative frequencies, altered haematopoiesis, impairments in antigen presentation, decreased B cell as well as T cell proliferation, a reduced TCR repertoire and defects in antibody production (Weiskopf et al., 2009). Ultimately these alterations result in a sharp decline in the response to new and persisting antigens and are referred to in the aggregate as immunosenescence. Thus it is not surprising that infectious diseases are one of the major causes of mortality in those over the age of 65 and that protective vaccination of the elderly is more difficult to establish than in younger individuals (Goodwin et al., 2006).

In one embodiment of the invention, the subject an elderly person (e.g. aged at least 60 years and over).

In another embodiment of the invention, the subject is a patient affected with any condition leading to immunodeficiency (immunosuppressive therapy, primary or secondary immunodeficiency) or a patient diagnosed with co-morbidity factors (such as chronic heart and pulmonary, metabolic and neurodegenerative diseases). In a particular embodiment, the patient is an HIV-infected patient. In another particular embodiment, the patient is affected with a chronic disease leading to an impaired immune function or immunosenescence such as a patient with diabetes including diabetes mellitus, a patient with chronic obstructive pulmonary disease (COPD) or a patient with sickle cell disease.

In another aspect, the invention relates to the use of hs-CRP and/or IL-6, I-FABP and at least one monocyte activation marker selected from the group consisting of sCD14 and sCD163 as a biomarker of impaired immune function or immunosenescence.

The term "biomarker", as used herein, refers generally to a molecule, i.e., a gene (or nucleic acid encoding said gene), protein, the expression of which in a biological sample from a patient can be detected by standard methods in the art (as well as those disclosed herein), and is predictive or denotes a condition of the patient from which it was obtained.

In a third aspect, the invention relates to an in vitro method for predicting the responsiveness of a subject to vaccination, comprising a step of determining the expression level of hs-CRP, I-FABP and at least one monocyte activation marker selected from the group consisting of sCD14 and sCD163 in a biological sample obtained from said subject.

In a further aspect, the invention relates to an in vitro method for predicting the responsiveness of a subject to vaccination, comprising a step of determining the expression level of hs-CRP and/or IL-6, I-FABP and at least one monocyte activation marker selected from the group consisting of sCD14 and sCD163 in a biological sample obtained from said subject.

The terms "active immunization" and "vaccination", as used herein, refer to the acquisition of immunologic memory and long-term protection against recurring diseases through antibody production in response to administration of an immunogenic antigen.

For instance, subjects may be immunized with a vaccine against a viral infectious disease such the influenza (flu) virus infection. The influenza vaccine, also known as flu shot, is an annual vaccination using a vaccine that is specific for a given year to protect against the highly variable influenza virus. Each seasonal influenza vaccine contains antigens representing three (trivalent vaccine) or four (quadrivalent vaccine) influenza virus strains: one influenza type A subtype H1N1 virus strain, one influenza type A subtype H3N2 virus strain, and either one or two influenza type B virus strains.

Methods for Determining the Expression Level of the Biomarkers of the Invention

Determination of the expression level of CRP and/or IL-6, I-FABP, sCD14 and/or sCD163 genes may be performed by a variety of techniques. Generally, the expression level as determined is a relative expression level. For example, the determination comprises contacting the biological sample with selective reagents such as probes or ligands, and thereby detecting the presence, or measuring the amount, of nucleic acids or polypeptides of interest originally in said biological sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

In a particular embodiment of the invention, the expression level of the CRP and/or IL-6, I-FABP, sCD14 and/or sCD163 genes may be determined by determining the quantity of mRNA.

Methods for determining the quantity of mRNA are well known in the art. For example the nucleic acid contained in the biological samples (e.g., peripheral blood mononuclear cells (PBMC) isolated from a blood sample obtained from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Quantitative or semi-quantitative RT-PCR is preferred. Real-time quantitative or semi-quantitative RT-PCR is particularly advantageous.

Nucleic acids having at least 10 nucleotides and exhibiting sequence complementarity or homology to the mRNA of interest herein find utility as hybridization probes. It is understood that such nucleic acids need not be identical, but are typically at least about 80% identical to the homologous region of comparable size, more preferably 85% identical and even more preferably 90-95% identical. Probes typically comprise single-stranded nucleic acids of between 10 to 1000 nucleotides in length, for instance of between 10 and 800, more preferably of between 15 and 700, typically of between 20 and 500. The probes and primers are "specific" to the nucleic acids they hybridize to, i.e. they preferably hybridize under high stringency hybridization conditions (corresponding to the highest melting temperature Tm, e.g., 50% formamide, 5x or 6xSCC. SCC is a 0.15 M NaCl, 0.015 M Na-citrate).

In the context of the invention, "hybridization" relates to the fact of obtaining a close interaction of the nucleotide probe and the target region that is expected to be revealed by the detection of the nucleotide probe. Such an interaction can be achieved by the formation of hydrogen bonds between the nucleotide probe and the target sequence, which is typical of the interactions between complementary nucleotide molecules capable of base pairing. Hydrogen bonds can be found, for example, in the annealing of two complementary strands of DNA.

It will be advantageous to use nucleic acids in combination with appropriate means, such as a detectable label, for detecting hybridization. A wide variety of appropriate indicators are known in the art including, fluorescent, radioactive, enzymatic or other ligands.

Conventional methods and reagents for isolating RNA from a sample comprise High Pure miRNA Isolation Kit (Roche), Trizol (Invitrogen), Guanidinium thiocyanate-phenol-chloroform extraction, PureLink™ miRNA isolation kit (Invitrogen), PureLink Micro-to-Midi Total RNA Purification System (invitrogen), RNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person.

In one embodiment, the expression level of one or more mRNAs is determined by the quantitative polymerase chain reaction (QPCR) technique. The QPCR may be performed using chemicals and/or machines from a commercially available platform. The QPCR may be performed using QPCR machines from any commercially available platform; such as Prism, geneAmp or StepOne Real Time PCR systems (Applied Biosystems), LightCycler (Roche), RapidCycler (Idaho Technology), MasterCycler (Eppendorf), BioMark™ HD System (Fluidigm), iCycler iQ system, Chromo 4 system, CFX, MiniOpticon and Opticon systems (Bio-Rad), SmartCycler system (Cepheid), RotorGene system (Corbett Lifescience), MX3000 and MX3005 systems (Stratagene), DNA Engine Opticon system (Qiagen), Quantica qPCR systems (Techne), InSyte and Syncrom cycler system (BioGene), DT-322 (DNA Technology), Exicycler Notebook Thermal cycler, TL998 System (lanlong), LineGene-K systems (Bioer Technology), or any other commercially available platform. The QPCR may be performed using chemicals from any commercially available platform, such as NCode EXPRESS qPCR or EXPRESS qPCR (Invitrogen), Taqman or SYBR green qPCR systems (Applied Biosystems), Real-Time PCR reagents (Eurogentec), iTaq mix (Bio-Rad), qPCR mixes and kits (Biosense), and any other chemicals, commercially available or not, known to the skilled person. The QPCR reagents and detection system may be probe-based, or may be based on chelating a fluorescent chemical into double-stranded oligonucleotides.

The QPCR reaction may be performed in a tube; such as a single tube, a tube strip or a plate, or it may be performed in a microfluidic card in which the relevant probes and/or primers are already integrated.

In a particular embodiment, the expression level of CRP and/or IL-6, I-FABP, sCD14 and/or sCD163 genes may be determined by determining of the quantity of protein encoded by the CRP, I-FABP, sCD14 and/or sCD163 genes.

Such methods comprise contacting the biological sample with a binding partner capable of selectively interacting with the protein present in said sample. The binding partner is generally an antibody that may be polyclonal or monoclonal, preferably monoclonal.

As used herein, the term "monoclonal antibody" refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the invention.

Laboratory methods for preparing monoclonal antibodies are well known in the art (see, for example, Harlow et al., 1988). Monoclonal antibodies (mAbs) may be prepared by immunizing purified CRP and/or IL-6, I-FABP, sCD14 and/or sCD163 into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody or aptamer, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or lndocyanine (Cy5)) to the antibody or aptamer, as well as indirect labelling of the probe or antibody by reactivity with a detectable substance. An antibody or aptamer of the invention may be labelled with a radioactive molecule by any method known in the art.

The aforementioned assays generally involve the coating of the binding partner (ie. antibody or aptamer) in a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

In another embodiment of the invention, the measurement of the biomarkers in the biological sample may be achieved by a cytometric bead array system wherein the antibodies that bind to the biomarkers are coated directly or indirectly on beads. Typically, Luminex® technology which is a new technology based on fluorescent detection using a flow cytometer, microbeads dyed with multiple fluorescent colours and lasers detection may be used. Thus, Luminex® Performance Assay Human CD14 Kit commercialized by R&D Systems, Inc may be used within the context of the invention.

For example, the level of a biomarker protein such as hs-CRP and/or IL-6, I-FABP, sCD14 and/or sCD163 may be measured by using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; Immunoelectrophoresis; immunoprecipitation.

Hs-CRP concentration may be measured by a C-reactive protein particle-enhanced immunoturbidimetric assay using latex-attached anti-CRP antibodies (i.e. Roche CRP Tinaquant®). Briefly, about 1.0 mL of patient sample serum is collected and stored in a plastic collection tube. Sample is placed into appropriate buffer, and anti-CRP antibody coupled to latex microparticles is added to the sample to start the reaction. These anti-CRP antibodies with conjugated latex microparticles react with antigen in the sample to form an antigen/antibody complex. Following agglutination, this is measured turbidimetrically using a Roche/Hitachi Modular P analyzer or a Siemens Advia 1650 analyzer.

More particularly, an ELISA method can be used, wherein the wells of a microtiter plate are coated with a set of antibodies against CRP and/or IL-6, I-FABP, sCD14 and/or sCD163. A biological sample containing or suspected of containing CRP and/or IL-6, I-FABP, sCD14 and/or sCD163 is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

ELISA useful for determining the expression level of I-FABP are well known from the skilled man in the art such as Quantikine® ELISA, Human FABP2/I-FABP Immunoassay commercialized by R&D Systems, Inc.

ELISA useful for determining the expression level of sCD14 are well known from the skilled man in the art such as the Quantikine® ELISA, Human sCD14 Immunoassay commercialized by R&D Systems, Inc.

ELISA useful for determining the amount of sCD163 are well known from the skilled man in the art such as the Quantikine® ELISA, Human sCD163 Immunoassay commercialized by R&D Systems, Inc.

Measuring the level of a biomarker protein such as CRP and/or IL-6, I-FABP, sCD14 and/or sCD163 (with or without immunoassay-based methods) may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, CRP and/or IL-6, I-FABP sCD14 and/or sCD163 may be identified based on the known "separation profile" e. g., retention time, for that protein and measured using standard techniques.

Alternatively, the separated proteins may be detected and measured by, for example, a mass spectrometer.

Methods for Adjusting a Treatment or a Vaccine

The invention further provides methods for developing personalized treatment plans. Information gained by way of the methods described above can be used to develop a personalized treatment plan for a patient identified as susceptible to nosocomial infections, with an immunosenescence profile and/or not responsive to vaccination according to the methods as above-described.

In a fourth aspect, the invention relates to a method for adjusting the anti-infective treatment administered to a patient susceptible to nosocomial infections, comprising the steps of: (i) performing the method for determining the patient's susceptibility to nosocomial infections of the invention, and (ii) adjusting the anti-infective treatment.

The methods can be carried out by, for example, using any of the determining the patient's susceptibility to nosocomial infections described above and, in consideration of the results obtained, designing a treatment plan for the patient. If susceptibility is determined, this indicates that said patient is at risk for a nosocomial infection. The ability to identify persons the most at risk of contracting a nosocomial infection would allow the setting up of better adapted and better targeted preventive therapy. Therefore, said patient is a candidate for the prophylaxis and/or treatment of nosocomial infections in general and of nosocomial bacterial infections in particular by using administering an anti-infective treatment such as an antibiotic. On the contrary, the absence of susceptibility is indicative of a reduced risk of nosocomial infection. Moreover, depending on the susceptibility, the patient may require a treatment regime that is more or less aggressive than a standard regimen, or it may be determined that the patient is best suited for a standard regimen.

Alternatively, the anti-infective treatment may consist of or include a personalized preventive management in order to minimize additional risks in a patient determined as at risk for a nosocomial infection: for instance by limiting patient exposure to invasive procedures (artificial ventilation, urinary and other catheterization), taking all the hygiene measures needed (single room, suitable balanced diet, etc . . . ).

In one embodiment of the invention, the nosocomial infection is a nosocomial bacterial infection and the anti-infective drug is an antibiotic.

As used herein, the term "antibiotic" refers to an antibacterial substance that helps an organism fight a bacterial infection.

Examples of antibiotics include, but are not limited to, the following large families: aminoglycosides, beta-lactams, such as cephalosporin beta-lactams, penicillin beta-lactams and other beta-lactams (carbapenems, monobactams), cyclines (doxycycline, limecycline, metacycline, minocycline, tetracycline, oxtetracycline, tigecycline), glycopeptides (teicoplanin, vancomycin) and polypeptides, macrolides and macrolide-like compounds (lincosamides, ketolides, streptogramins), quinolones, including fluoroquinolones, antibacterial peptides, in particular gramicidin, phages, and others (fusidic acid, noxytiolin, daptomycin, fosfomycin, oxazolidinone, phenicols, polymyxins, rifampicin, etc.).

In a fifth aspect, the invention relates to a method for adjusting the vaccination regime and/or dosing administered to a subject, comprising the steps of: (i) performing the method predicting the responsiveness of a subject to vaccination of the invention, and (ii) adjusting the doses of vaccine.

In one embodiment of the invention, the vaccination is against an infectious disease such as viral infectious diseases. Examples of viral infectious disease include, but are not limited to, AIDS, Respiratory Syncytial Virus (RSV), Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV, Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease and Yellow fever.

The methods can be carried out by, for example, using any of the determining the predicting the responsiveness of a subject to vaccination described above and, in consideration of the results obtained, designing a treatment plan for the patient.

Depending on the efficacy of the vaccine of interest (such as the efficacy of the influenza vaccine) and hence the subject is or not responsive to the vaccination, the subject may require a vaccination regime and/or dosing that is more important than a standard regimen, or it may be determined that the patient is best suited for a standard regimen.

In one embodiment of the invention, the subject is a subject unprimed against influenza, either being naive, or having failed to respond previously to influenza infection or vaccination. Suitably the subject is an elderly person (e.g. aged at least 60 years and over).

In another embodiment of the invention, the subject is a patient affected with any condition leading to immunodeficiency (immunosuppressive therapy, primary or secondary immunodeficiency) or a patient diagnosed with co-morbidity factors (such as chronic heart and pulmonary, metabolic and neurodegenerative diseases). In a particular embodiment, the patient is an HIV-infected patient. In another particular embodiment, the patient is affected with a chronic disease leading to an impaired immune function or immunosenescence such as a patient with diabetes including diabetes mellitus, a patient with chronic obstructive pulmonary disease (COPD) or a patient with sickle cell disease.

Standards are applied internationally to measure the efficacy of influenza vaccines. Serological variables are assessed according to criteria of the European Agency for the Evaluation of Medicinal Products for human use (CHMP/BWP/214/96, Committee for Proprietary Medicinal Products (CPMP). Note for harmonization of requirements for influenza vaccines, 1997. CHMP/BWP/214/96 circular N° 96-0666: 1-22) for clinical trials related to annual licensing procedures of influenza vaccines (Table below).

| CHMP criteria | | |
|---|---|---|
| | 18-60 years | >60 years |
| Seroconversion rate* | >40% | >30% |
| Conversion factor** | >2.5 | >2.0 |
| Protection rate*** | >70% | >60% |

*Seroconversion rate is defined as the proportion of subjects in each group having a protective post-vaccination titre >1:40. The seroconversion rate simply put is the % of subjects who have an HI titre before vaccination of <1:10 and >1:40 after vaccination. However, if the initial titre is >1:10 then there needs to be at least a fourfold increase in the amount of antibody after vaccination.
**Conversion factor is defined as the fold increase in serum HI geometric mean titres (GMTs) after vaccination, for each vaccine strain.
***Protection rate is defined as the proportion of subjects who were either seronegative prior to vaccination and have a (protective) post-vaccination HI titre of >1:40 or who were seropositive prior to vaccination and have a significant 4-fold increase in titre post-vaccination; it is normally accepted as indicating protection.

The requirements are different for adult populations (18-60 years) and elderly populations (>60 years). For interpandemic influenza vaccines, at least one of the assessments (seroconversion factor, seroconversion rate, seroprotection rate) should meet the European requirements, for all strains of influenza included in the vaccine.

Kits of the Invention

In a sixth aspect, the invention relates to an a kit suitable for performing the methods of the invention wherein said kit comprises means for measuring the expression levels of hs-CRP, I-FABP and at least one monocyte activation marker selected from the group consisting of sCD14 and sCD163.

In a further, the invention relates to an a kit suitable for performing the methods of the invention wherein said kit comprises means for measuring the expression levels of hs-CRP and/or IL-6, I-FABP and at least one monocyte activation marker selected from the group consisting of sCD14 and sCD163.

In one embodiment of the invention, the kit comprises labelled antibodies binding to hs-CRP and/or IL-6, I-FABP and at least one monocyte activation marker selected from the group consisting of sCD14 and sCD163.

The invention will be further illustrated by the following figures and examples. However, these examples and figures should not be interpreted in any way as limiting the scope of the present invention.

Example: Association of High Plasma Levels of hs-CRP, IL-6, I-FABP and sCD14 Identifies Older Patients at High Risk of Developing Healthcare-Associated Infections Methods
Study Design
We used data from a previously described (Laurent M, Bories P N, Le Thuaut A, Liuu E, Ledudal K, Bastuji-Garin S, et al. Impact of comorbidities on hospital-acquired infections in a geriatric rehabilitation unit: prospective study of 252 patients. J Am Med Dir Assoc. October 2012; 13(8): 760.e7-12) prospective cohort study conducted between July 2006 and November 2008 in a teaching hospital (1300 beds) in the Paris area, France. The cohort comprised 252 consecutive Caucasians aged 75 years or over who were referred to a geriatric rehabilitation unit by acute medical or surgical units during the study period. Inclusion criteria were medically stable status at admission; need for long-term care and rehabilitation; and absence of terminal disease (e.g., uncontrolled malignancy or severe dementia), fever, infection, cancer, or known immunological dysfunction. Patients treated with corticosteroids or immunosuppressants and those who stayed less than 48 hours in the rehabilitation unit were not eligible. Patients were followed up until discharge from the rehabilitation unit or up to 3 months after inclusion. The 121 patients for whom baseline serum samples were still available were included in the present study. The study was approved by the Ile-de-France IX ethics committee in Paris, France (#SCR06010). Written informed consent was obtained from each patient before inclusion in the cohort.

Assessment of Hospital-Acquired Infections

As previously described, HAI was defined as a well-documented infection that was neither present nor incubating at admission and that met the Centers for Disease Control definition of nosocomial infection (Garner J S, Jarvis W R, Emori T G, Horan T C, Hughes J M. CDC definitions for nosocomial infections, 1988. Am J Infect Control. juin 1988; 16(3):128-40). The procedure for ascertaining HAIs is described in the Supplementary Material.

Data Collection

Technicians blinded to patient status assayed hs-CRP, IL-6, I-FABP, and sCD14 in baseline serum samples. For each patient, the two main known risk factors for HAIs—comorbidities and invasive procedures—were collected routinely on a standardized form.

Statistical Analysis

Qualitative variables were described as number (%) and compared using the $Chi^2$-test or Fisher exact test, as appropriate. Quantitative variables were described as median [25th-75th percentiles] and compared using the nonparametric Mann-Whitney test. We compared the groups with and without HAI regarding the following baseline characteristics: comorbidities (CIRS-G score), invasive procedures, and levels of the four laboratory markers (hs-CRP, IL6, I-FABP, and sCD14) (Table 1). Univariate odds ratios (OR) were estimated with their 95% confidence intervals (95% CIs) using logistic regression models. Because of their skewed distribution, CIRS-G, hs-CRP, IL6, I-FABP, and sCD14 were log-transformed; the ORs and 95% CIs are given for a 1-standard deviation (SD) variation in the log-transformed values. Pairwise analyses were performed to assess interactions and confounding by fitting multiplicative models. When a significant interaction was found, a composite variable was built. For this step, quantitative variable values were categorized as below or within the highest quartile (Q3; coded 0 and 1, respectively) or as below or above the median value (Q2; coded 0 and 1, respectively), as appropriate. Since both hs-CRP and IL-6 are inflammatory markers, we considered two separate models, one combining hs-CRP, I-FABP, and sCD14 and the other using IL-6 instead of hs-CRP. Then, we used multivariate modeling to assess whether these markers were associated with the HAI risk independently from comorbidities and invasive procedures.

A sensitivity analysis was performed among patients who stayed at least 5 days in the rehabilitation unit, under the hypothesis that the 48-hour stay required for the main analysis might be too short for HAIs to become symptomatic.

All tests were two-sided, and P values ≤0.05 were considered significant. No adjustments for multiple comparisons were performed. Data were analyzed using STATA software SE12.0 (StataCorp, College Station, Tex.).

Results

Baseline Characteristics

Table 1 displays the baseline characteristics of the 121 patients. Their mean length of stay in the rehabilitation unit was 45 days (range, 3-91). At least one HAI was diagnosed in 62 patients. The most common sites of HAI were the respiratory tract (50%; 31/62) and urinary tract (38.7%; 24/62). The median time to HAI diagnosis after admission to the rehabilitation unit was 12 days (range, 2-62).

Comorbidities and invasive procedures were significantly associated with subsequent HAI, while baseline leukocyte count was not.

Associations Linking Baseline Biomarker Levels to Subsequent Hospital-Acquired Infection (HAI)

Baseline levels of hs-CRP, IL6 and s-CD14 were significantly associated with HAI occurrence (P<0.05), while only a trend for an association was observed for I-FABP (Table 1).

Identification of Patients at High Risk for Healthcare-Associated Infections (HAIs)

In joint analyses, a significant third-order interaction was observed for serum hs-CRP, I-FABP, and sCD14 levels; as well as two-order interactions for each of the three pairs formed by these three variables. Therefore, we built composite variables combining hs-CRP (≥Q2 versus <Q2), I-FABP (≥Q3 versus <Q3), and sCD14 (≥Q2 versus <Q2). Because the HAI risk was lower in patients with hs-CRP values below the median value, irrespective of their I-FABP and sCD14 levels, all these patients were pooled in the reference category. As shown in Table 2 (model 1), hs-CRP elevation was associated with a significantly higher HAI risk when the I-FABP level was in the highest quartile (OR, 4; 95% CI, 1.39-11.49; P=0.010).

We then considered both I-FABP and sCD14 levels (Table 2, model 2). The patients with high levels of all three markers had an 11-fold higher risk of HAI (OR, 10.8; 95% CI, 2.28-51.1; P=0.003). In contrast, combined hs-CRP and I-FABP elevation without sCD14 elevation was not associated with a significantly higher HAI risk.

When we substituted IL-6 for hs-CRP as the marker for low-grade inflammation, the results were unchanged (Table 2, model 2): IL-6 elevation (>median) was associated with a significantly higher HAI risk when the I-FABP level was in the highest quartile, and patients with high levels of all three markers had a 6-fold higher HAI risk.

We suggest the term "biomarker risk profile" to designate the combination of high hs-CRP or IL-6, I-FABP, and sCD14 levels.

Association between the Biomarker Risk Profile and the Risk of Healthcare-Associated Infections (HAIs)

We previously reported that comorbidities and invasive procedures were major risk factors for HAIs (Plonquet A, Bastuji-Garin S, Tahmasebi F, Brisacier C, Ledudal K, Farcet J, et al. Immune risk phenotype is associated with nosocomial lung infections in elderly in-patients. Immun Ageing A. 2011; 8:8). Adjusting for these two factors in the multivariate analysis had little effect on our results: the biomarker risk profile using hs-CRP remained associated with a 10-fold higher HAI risk after adjustment for dependency according to CIRS-G criteria or for invasive procedures (Table 3, model 1). Likewise, the biomarker risk profile using IL-6 remained associated with a 5-fold higher HAI risk after adjustment for dependency according to CIRS-G criteria or for invasive procedures (Table 3, model 2).

Sensitivity Analysis

Analyses performed among the 100 patients who stayed at least 5 days in the rehabilitation unit produced closely similar results (Table 4). The biomarker risk profile with hs-CRP was associated with a 13-fold higher risk of HAI and remained associated with the HAI risk after adjustment for dependency according to CIRS-G criteria or for procedures.

TABLE 1

Baseline characteristics of the overall study population (N = 121) and of the subgroups with and without healthcare-associated infections (univariate analyses)

|  | Overall (N = 121) | Healthcare-associated infection | | Univariate | |
| --- | --- | --- | --- | --- | --- |
|  |  | No 59 (48.8%) | Yes 62 (51.2%) | analysis OR (95% CI) | P value[a] |
| General characteristics |  |  |  |  |  |
| Age, median (Q1-Q3), years | 84 (81-90) | 84 (80-90) | 85.5 (81-89) | 1.01 (0.95-1.08) | 0.77 |
| Female gender, N (%) | 91 (75.2) | 45 (76.3) | 46 (74.2) | 0.89 (0.39-2.04) | 0.79 |
| Invasive procedures, N (%) | 38 (31.4) | 9 (15.3) | 29 (46.8) | 4.88 (2.05-11.62) | <0.001 |
| CIRS-G, median (Q1-Q3) | 11 [10-14] | 10 [9-13] | 13 [10-15] | 1.84 (1.20-2.82) | 0.005 |
| Biological parameters |  |  |  |  |  |
| White blood cells (×10$^6$/L) | 6.9 (5.6-8.3) | 6.5 (5.6-8.0) | 7.2 (5.7-8.6) | 1.11 (0.83-1.48) | 0.18 |
| hs-CRP (mg/L), median (Q1-Q3) | 6.43 (2.11-13) | 6.02 (1.51-11) | 6.59 (4.23-13.43) | 1.54 (1.02-2.33) [b] | 0.047 |
| IL6 (pg/mL), median (Q1-Q3) | 5.70 (3.14-9.86) | 4.99 (2.67-9.46) | 6.30 (4.34-10.27) | 1.47 (1.02-2.12) [b] | 0.04 |

TABLE 1-continued

Baseline characteristics of the overall study population (N = 121) and of the subgroups with and without healthcare-associated infections (univariate analyses)

|  | Overall (N = 121) | Healthcare-associated infection No 59 (48.8%) | Healthcare-associated infection Yes 62 (51.2%) | Univariate analysis OR (95% CI) | P value[a] |
|---|---|---|---|---|---|
| I-FABP (pg/mL), median (Q1-Q3) (n = 2) | 1428 (951-2455) | 1413 (938-2004) | 1510 (1037-3057) | 1.50 (1.00-2.24) [b] | 0.06 |
| sCD14 (µg/mL), median (Q1-Q3) (n = 9) | 0.68 (0.60-0.77) | 0.65 (0.58-0.75) | 0.71 (0.61-0.81) | 1.55 (1.11-2.16) [b] | 0.02 |

Abbreviations:
OR, odds ratio;
95% CI, 95% confidence interval;
CIRS-G, Cumulative Illness Rating Scale for Geriatrics;
N, number of patients;
Q1-Q3, 25th-75th percentile;
hs-CRP, high sensitivity C-reactive protein;
(n=), number of patients with missing data
[a] P value obtained using the nonparametric Mann-Whitney test, Chi2 test, or Fisher's exact test, as appropriate
[b] Odds ratios were computed for an increase by 1 standard deviation in the log-transformed values.

TABLE 2

Risk of healthcare-associated infections according to the hs-CRP, I-FABP, and sC14 serum levels (univariate analyses using logistic regression models)

| Hs-CRP < Q2 (6.02 mg/L) | | Model 1[b] OR 95% CI | Model 1[b] P value | | Model 2[b] OR 95% CI | Model 2[b] P value |
|---|---|---|---|---|---|---|
| N = 55 HAI: 25 (45.5%) | | 1 (reference category) | | | 1 (reference category) | |
| CRP ≥ Q2 N = 62 HAI: 37 (59.7%) | I-FABP Q < 3 (2004 pg/L) N = 36 HAI: 17 (47.2%) | 0.89 [0.39-2.02] | 0.78 | sCID14 < Q2 (0.65 µg/mL) N = 14 HAI: 5 (35.7%) | 0.67 [0.20-2.25] | 0.51 |
|  |  |  |  | sCD14 ≥ Q2 N = 22 HAI: 11 (50.0%) | 1.44 [0.53-3.89] | 0.47 |
|  | I-FABP ≥ Q3 N = 26 HAI: 20 (76.9%) | 4.00 [1.39-11.49] | 0.01 | sCD14 < Q2 N = 6 HAI: 2 (33.3%) | 0.60 [0.12-3.55] | 0.57 |
|  |  |  |  | sCD14 ≥ Q2 N = 20 HAI: 18 (90%) | 10.80 [2.28-51.1][b] | 0.003 |

| Sensitivity analysis using IL6 instead of hs-CRP to assess low grade inflamation | | | | | | |
|---|---|---|---|---|---|---|
| IL6 < Q2 (4.99 pg/L) N = 52 HAI: 22 (42.3%) | | 1 (reference category) | | | 1 (reference category) | |
| IL6 ≥ Q2 N = 63 HAI: 38 (60.3%) | I-FABP < Q3 (2004 pg/L) N = 36 HAI: 18 (50%) | 1.24 [0.55-2.80] | 0.61 | sCID14 < Q2 (0.65 µg/mL) N = 15 HAI: 6 (40%) | 0.91 [0.28-2.93] | 0.87 |
|  |  |  |  | sCD14 ≥ Q2 N = 21 HAI: 12 (57.1%) | 1.82 [0.65-5.06] | 0.25 |
|  | I-FABP ≥ Q3 N = 27 HAI: 20 (74.1%) | 6.90 [1.40-10.82] | 0.009 | sCD14 < Q2 N = 5 HAI: 2 (40%) | 0.91 [0.14-5.91] | 0.92 |
|  |  |  |  | sCD14 ≥ Q2 N = 22 HAI: 18 (81.8%) | 6.14 [1.82-20.68] | 0.003 |

Abbreviations:
hs-CRP, high sensitivity C-reactive protein;
I-FABP, intestinal fatty acid-binding protein;
sCD14, soluble CD14;
OR, odds ratio;
95% CI, 95% confidence interval;
N, number of patients;
Q2, median value;
Q3, 75th percentile
[a] Model 1 takes into account a combination of hs-CRP (IL6) and I-FABP levels coded as follows: 0 if hs-CRP (/)IL6) < Q2 whatever the I-FABP level; 1 if hs-CRP (/)IL6 ≥ Q2, and I-FAPB < Q3; and 2 if hs-CRP (IL6) ≥ Q2 and I-FABP ≥ Q3.
[b] Model 2 takes into account a combination of hs-CRP (IL6), I-FABP, and sCD14 levels coded as follows: 0 if hs-CRP (IL6) < Q2 whatever the I-FABP and sCD14 levels; 1 if hs-CRP (IL6) ≥ Q2, I-FAPB < Q3, and sCD14 < Q2; 2 if hs-CRP (IL6) ≥ Q2, I-FABP < Q3, and sCD14 ≥ Q2; 3 if hs-CRP (IL6) ≥ Q2, I-FABP ≥ Q3, and sCD14 < Q2; and 4 if hs-CRP (IL6) ≥ Q2, I-FABP ≥ Q3, and sCD14 ≥ Q2.

TABLE 3

Risk of healthcare-associated infections according to the CRP, I-FABP and sCD14 serum levels adjusted for major risk factors for healthcare-associated infections (multivariate logistic regression analyses)

| | OR (95% CI) | P value |
|---|---|---|
| Model with invasive procedures [a] | | |
| Invasive procedures [b] | 4.70 (1.84-12.01) | 0.001 |
| hs-CRP ≥ Q2, I-FABP ≥ Q3, and sCD14 ≥ Q2 | 9.62 (2.04-45.4) | 0.004 |
| Model with CIRS-G [a] | | |
| CIRS-G | 1.14 (1.01-1.28) | 0.029 |
| hs-CRP ≥ Q2, I-FABP ≥ Q3, and sCD14 ≥ Q2 | 9.45 (2.05-43.69) | 0.004 |
| Sensitivity analysis using IL6 instead of hs-CRP to assess low-grade inflammation | | |
| Model with invasive procedures [a] | | |
| Invasive procedures [b] | 4.83 (1.90-12.27) | 0.001 |
| IL6 ≥ Q2, I-FABP ≥ Q3 and sCD14 ≥ Q2 | 5.0 (1.50-16.64) | 0.009 |
| Model with CIRS-G [a] | | |
| CIRS-G | 1.15 (1.02-1.29) | 0.024 |
| IL6 ≥ Q2, I-FABP ≥ Q3, and sCD14 ≥ Q2 | 4.68 (1.44-15.7) | 0.01 |

Abbreviations:
OR, odds ratio; 95%
CI, 95% confidence interval;
hs-CRP, high-sensitivity C-reactive protein;
CIRS-G, Cumulative Illness Rating Scale for Geriatrics;
Q2, median value;
Q3, 75th percentile

[a] For these models, instead of using the previous combinations of hs-CRP (IL6), I-FABP, and sCD14 levels (hs-CRP (IL6) < Q2 whatever the I-FABP and sCD14 levels; hs-CRP (IL6) ≥ Q2, I-FAPB < Q3, and sCD14 < Q2; hs-CRP (IL6) ≥ Q2, I-FABP < Q3, and sCD14 ≥ Q2; hs- CRP (IL6) ≥ Q2, I-FABP ≥ Q3, and sCD14 < Q2; and hs-CRP (IL6) ≥ Q2, I-FABP ≥ Q3, and sCD14 ≥ Q2), we compared hs-CRP(IL6) ≥ Q2, I-FAPB ≥ Q3, and sCD14 ≥ Q2 versus all other combinations pooled.
[b] Invasive procedures recorded for each patient until HAI occurred or the patient was discharged from the rehabilitation unit included intravenous catheter, indwelling urinary catheter, intermittent urinary catheter, gastrointestinal tract endoscopy, nasogastric tube, colonoscopy, and bronchoscopy.

TABLE 4

Risk of healthcare-associated infections according to the hs-CRP, I-FABP, and sCD14 serum levels among the 100 patients who stayed at lease five days in the rehabilitatation unit (univariate and multivariate analyses using logistic regression models)

| Hs-CRP < Q2 (4.8 mg/L) | | Model 1[a] | | | Model 2[b] | |
|---|---|---|---|---|---|---|
| | | OR 95% CI | P value | | OR 95% CI | P value |
| N = 40 HAI: 15 (37.5%) | | 1 (reference category) | | | 1 (reference category) | |
| CRP ≥ Q2 N = 57 HAI: 34 (59.6%) | I-FABP < Q3 (2106 pg/L) N = 32 HAI: 15 (46.9%) | 1.40 [0.56-3.53] | 0.47 | sCID14 < Q2 (0.65 µg/mL) N = 11 HAI: 5 (35.7%) | 0.95 [0.24-3.81] | 0.95 |
| | | | | sCD14 ≥ Q2 N = 21 HAI: 11 (52.4%) | 1.83 [0.63-5.34] | 0.27 |
| | I-FABP ≥ Q3 N = 25 HAI: 19 (76.0%) | 5.28 [1.72-16.16] | 0.004 | sCD14 < Q2 N = 7 HAI: 3 (42.9%) | 1.25 [0.25-6.37] | 0.5779 |
| | | | | sCD14 ≥ Q2 N = 18 HAI: 16 (88.9%) | 13.33 [2.68-66.26] | 0.002 |

| Multivariate analyses | OR (95% CI) | P value |
|---|---|---|
| Model with invasive procedure[c] | | |
| At least 1 invasive procedure[d] | 6.78 (2.32-19.84) | <0.001 |
| Hs-CRP ≥ Q2, I-FABP ≥ Q3, and sCD14 ≥ Q2 | 11.27 (2.29-55.45) | 0.003 |
| Model with CIRS-G[c] | | |
| CIRS-G | 1.14 (1.00-1.30) | 0.47 |
| Hs-CRP ≥ Q2, I-FABP ≥ Q3, and sCD14 ≥ Q2 | 9.82 (2.08-46.44) | 0.004 |

Abbreviations:
hs-CRP, high sensitivity C-reactive protein;
I-FABP, intestinal fatty acid-binding protein;
sCD14, soluble CD14;
OR, odds ratio;
95% CI, 95% confidence interval;
N, number of patients;
Q2, median value;
Q3, 75th percentile;
CIRS-G, Cumulative Illness Rating Scale for Geriatrics

TABLE 4-continued

Risk of healthcare-associated infections according to the hs-CRP, I-FABP, and sCD14 serum levels among the 100 patients who stayed at lease five days in the rehabilitatation unit (univariate and multivariate analyses using logistic regression models)

[a] Model 1 takes into account a combination of hs-CRP (IL6) and I-FABP levels coded as follows: 0 if hs-CRP (/)IL6) < Q2 whatever the I-FABP level; 1 if hs-CRP (/)IL6 ≥ Q2 and I-FAPB < Q3; and 2 if hs-CRP (IL6) ≥ Q2 and I-FABP ≥ Q3.
[b] Model 2 takes into account a combination of hs-CRP (IL6), I-FABP, and sCD14 levels coded as follows: 0 if hs-CRP (IL6) < Q2 whatever the I-FABP and sCD14 levels; 1 if hs-CRP (IL6) ≥ Q2, I-FAPB < Q3, and sCD14 < Q2; 2 if hs-CRP (IL6) ≥ Q2, I-FABP < Q3, and sCD14 ≥ Q2; 3 if hs-CRP (IL6) ≥ Q2, I-FABP ≥ Q3, and sCD14 < Q2; and 4 if hs-CRP (IL6) ≥ Q2, I-FABP ≥ Q3, and sCD14 ≥ Q2.
[c] For these models, instead of using the previous combinations of hs-CRP (IL6), I-FABP, and sCD14 levels, we compared hs-CRP (IL6) ≥ Q2, I-FAPB ≥ Q3, and sCD14 ≥ Q2 versus all other combinations pooled.
[d] Invasive procedures recorded for each patient until HAI occurred or the patient was discharged from the rehabilitation unit included intravenous catheter, indwelling urinary catheter, intermittent urinary catheter, gastrointestinal tract endoscopy, nasogastric tube, colonoscopy, and bronchoscopy.

DISCUSSION

We assessed whether biomarkers for inflammation associated with microbial translocation predicted the risk of HAI. In patients aged 75 years or over and admitted to a geriatric rehabilitation unit, concomitant elevations in the levels of three biomarkers—hs-CRP, I-FABP, and sCD14—were associated with a 11-fold higher risk of HAI. Adjustment on two known risk factors, comorbidities and invasive procedures did not change the associations linking the three markers to the HAI risk. Using another inflammatory marker, IL-6, we obtained closely similar results, suggesting that this biomarker risk profile may help to identify patients at high risk for HAI.

Immunosenescence is a multifactorial process of which one component is low-level inflammation, known as inflammaging. Our study supports microbial translocation as a contributor to the increased HAI risk observed in older individuals. Thus, patients with high levels of hs-CRP or IL-6 and of I-FABP exhibited a 4-fold higher risk of HAI. Microbial translocation plays a key role in driving persistent immune activation, as shown in HIV-infected patients (Brenchley J M, Douek D C. Microbial translocation across the GI tract. Annu Rev Immunol. 2012; 30:149-73). Aging may induce intestinal-barrier disruption comparable to that caused by the HIV. Thus, aging epithelial cells have mitochondrial mutations that affect their progeny in the mucosa (Saffrey M J. Aging of the mammalian gastrointestinal tract: a complex organ system. Age Dordr Neth. juin 2014; 36(3): 9603), and aging is associated with remodeling of the tight junctions between epithelial cells (Tran L, Greenwood-Van Meerveld B. Age-associated remodeling of the intestinal epithelial barrier. J Gerontol A Biol Sci Med Sci. sept 2013; 68(9):1045-56). The local control of microorganisms that cross the intestinal barrier may also be compromised by many age-related immunological alterations such as impaired chemotaxis and phagocytosis, altered expression of pattern recognition receptors (PRR), activation of these receptors by endogenous ligands associated with cellular damage, and aberrant signaling events downstream of PRR activation resulting in cytokine secretion (Shaw A C, Goldstein D R, Montgomery R R. Age-dependent dysregulation of innate immunity. Nat Rev Immunol. déc 2013; 13(12): 875-87).

High plasma sCD14 was one of the three components of the biomarker risk profile identified in our study. Plasma sCD14 levels reflect monocyte activation. LPS, found in the membrane of Gram-negative bacteria, is a potent monocyte activator that binds to CD14 and induces the shedding of sCD14. In previous studies, sCD14 levels were associated with a high risk of future clinical cardiovascular disease in older adults (Reiner A P, Lange E M, Jenny N S, Chaves P H M, Ellis J, Li J, et al. Soluble CD14: genomewide association analysis and relationship to cardiovascular risk and mortality in older adults. Arterioscler Thromb Vasc Biol. jany 2013; 33(1):158-64) and a high risk of mortality in gram-negative septic shock (Landmann R, Zimmerli W, Sansano S, Link S, Hahn A, Glauser M P, et al. Increased circulating soluble CD14 is associated with high mortality in gram-negative septic shock. J Infect Dis. mars 1995; 171 (3):639-44). In another study, LPS-binding protein, another biomarker of microbial translocation, was associated with physical function in healthy older adults, while sCD14 was associated with several inflammatory markers but not with physical function (Stehle J R, Leng X, Kitzman D W, Nicklas B J, Kritchevsky S B, High K P. Lipopolysaccharide-binding protein, a surrogate marker of microbial translocation, is associated with physical function in healthy older adults. J Gerontol A Biol Sci Med Sci. November 2012; 67(11):1212-8).

In our study, I-FABP elevation consistent with intestinal barrier disruption was associated with the HAI risk only when sCD14 was also elevated, indicating monocyte activation, i.e., penetration of intestinal microorganisms and/or their products into the systemic circulation. In patients with high hs-CRP and I-FABP levels but low sCD14 levels, the HAI risk was similar to that in patients with normal hs-CRP levels. This finding suggests that intestinal barrier disruption may lead to microbial translocation only if the local immune system is deficient. Secretory IgA antibody on mucosal surfaces plays a pivotal role in controlling the microbiota (Macpherson A J, Geuking M B, McCoy K D. Homeland security: IgA immunity at the frontiers of the body. Trends Immunol. avr 2012; 33(4):160-7). Deficient IgA production has been reported in elderly individuals (Sato S, Kiyono H, Fujihashi K. Mucosal Immunosenescence in the Gastrointestinal Tract: A Mini-Review. Gerontology. 2015; 61(4): 336-42.). The combination of intestinal barrier disruption and impaired intestinal wall immunity may generate chronic low-level systemic inflammation, which may in turn affect immune response regulation, resulting in an increased risk of HAIs. Finally, in patients with high hs-CRP but normal I-FABP levels, other mechanisms may be active, leading to different outcomes.

We used two strategies to test the robustness of our findings. First, we repeated the analysis after replacing hs-CRP with IL6, an inflammatory marker associated with inflammaging in the general population (Michaud M, Balardy L, Moulis G, Gaudin C, Peyrot C, Vellas B, et al. Proinflammatory cytokines, aging, and age-related diseases. J Am Med Dir Assoc. déc 2013; 14(12):877-82.). Patients with high levels of IL-6, I-FABP, and sCD14 had a 6-fold higher HAI risk. Furthermore, the biomarker risk profile with IL-6 remained associated with a 5-fold higher HAI risk after adjustment for dependency or invasive procedures. These results support a link between microbial translocation and low-grade inflammation. Second, we confined the analysis to patients who stayed at least 5 days in the rehabilitation unit. The 48-hour stay required for the main analysis may be too short for HAIs to become symptomatic in patients coming from acute care units. Again, the results were essentially unchanged, with a 13-fold higher HAI risk among patients with high levels of all three markers. Moreover, mean time to HAI diagnosis was 12 days. These data suggest that elevation of the three markers at admission was linked to low-grade chronic inflammation. We are not aware of previous reports that a biomarker risk profile is strongly associated with HAIs in patients 75 years or older. Whether routine assessment of this profile followed by intensified prevention and monitoring if positive diminishes the morbidity and mortality rates associated with HAIs deserves investigation.

CONCLUSION

This study identified a biomarker risk profile strongly associated with HAIs in patients 75 years or older who were admitted to a rehabilitation unit. The profile involves three biomarkers, hs-CRP or IL-6 for systemic inflammation, I-FABP for intestinal-barrier disruption, and sCD14 for systemic monocyte activation.

Our findings support a link between microbial translocation and the low-grade inflammation seen in some older patients with HAI and identify a combination of biomarkers as a risk factor for HIA. More research is needed to elucidate the role for low-grade inflammation and microbial translocation in HAIs. However, from a clinical stand-point, our findings suggest that the three biomarkers may help identify those individuals most at risk for HAI.

REFERENCES

Throughout this application, various references describe the state of the art to which this invention pertains. The disclosures of these references are hereby incorporated by reference into the present disclosure.
1. Magill, S. S., Edwards, J. R., Fridkin, S. K. & Emerging Infections Program Healthcare-Associated Infections and Antimicrobial Use Prevalence Survey Team. Survey of health care-associated infections. *N. Engl. J. Med.* 370, 2542-2543 (2014).
2. Zimlichman, E. et al. Health care-associated infections: a meta-analysis of costs and financial impact on the US health care system. *JAMA Intern. Med.* 173, 2039-2046 (2013).
3. Emori, T. G. et al. Nosocomial infections in elderly patients in the United States, 1986-1990. National Nosocomial Infections Surveillance System. *Am. J. Med.* 91, 289S-293S (1991).
4. Laurent, M. et al. Impact of comorbidities on hospital-acquired infections in a geriatric rehabilitation unit: prospective study of 252 patients. *J. Am. Med. Dir. Assoc.* 13, 760.e7-12 (2012).
5. Goronzy, J. J. & Weyand, C. M. Understanding immunosenescence to improve responses to vaccines. *Nat. Immunol.* 14, 428-436 (2013).
6. Panda, A. et al. Human innate immunosenescence: causes and consequences for immunity in old age. *Trends Immunol.* 30, 325-333 (2009).
7. Hakim, F. T., Flomerfelt, F. A., Boyiadzis, M. & Gress, R. E. Aging, immunity and cancer. *Curr. Opin. Immunol.* 16, 151-156 (2004).
8. Derhovanessian, E., Larbi, A. & Pawelec, G. Biomarkers of human immunosenescence: impact of Cytomegalovirus infection. *Curr. Opin. Immunol.* 21, 440-445 (2009).
9. Pawelec, G., Ferguson, F. G. & Wikby, A. The SENIEUR protocol after 16 years. *Mech. Ageing Dev.* 122, 132-134 (2001).
10. Strindhall, J. et al. No Immune Risk Profile among individuals who reach 100 years of age: findings from the Swedish NONA immune longitudinal study. *Exp. Gerontol.* 42, 753-761 (2007).
11. Plonquet, A. et al. Immune risk phenotype is associated with nosocomial lung infections in elderly in-patients. *Immun. Ageing A* 8, 8 (2011).
12. Shaw, A. C., Goldstein, D. R. & Montgomery, R. R. Age-dependent dysregulation of innate immunity. *Nat. Rev. Immunol.* 13, 875-887 (2013).
13. Viola, J. & Soehnlein, O. Atherosclerosis—A matter of unresolved inflammation. *Semin. Immunol.* 27, 184-193 (2015).
14. Serpente, M., Bonsi, R., Scarpini, E. & Galimberti, D. Innate immune system and inflammation in Alzheimer's disease: from pathogenesis to treatment. *Neuroimmunomodulation* 21, 79-87 (2014).
15. Klatt, N. R., Chomont, N., Douek, D. C. & Deeks, S. G. Immune activation and HIV persistence: implications for curative approaches to HIV infection. *Immunol. Rev.* 254, 326-342 (2013).
16. Brenchley, J. M. & Douek, D. C. Microbial translocation across the GI tract. *Annu. Rev. Immunol.* 30, 149-173 (2012).
17. Sandler, N. G. & Douek, D. C. Microbial translocation in HIV infection: causes, consequences and treatment opportunities. *Nat. Rev. Microbiol.* 10, 655-666 (2012).
18. Tran, L. & Greenwood-Van Meerveld, B. Age-associated remodeling of the intestinal epithelial barrier. *J. Gerontol. A. Biol. Sci. Med. Sci.* 68, 1045-1056 (2013).
19. Pelsers, M. M. A. L. et al. Intestinal-type and liver-type fatty acid-binding protein in the intestine. Tissue distribution and clinical utility. *Clin. Biochem.* 36, 529-535 (2003).
20. Shozushima, T. et al. Usefulness of presepsin (sCD14-ST) measurements as a marker for the diagnosis and severity of sepsis that satisfied diagnostic criteria of systemic inflammatory response syndrome. *J. Infect. Chemother. Off. J. Jpn. Soc. Chemother.* 17, 764-769 (2011).
21. Ulla, M. et al. Diagnostic and prognostic value of presepsin in the management of sepsis in the emergency department: a multicenter prospective study. *Crit. Care Lond. Engl.* 17, R168 (2013).

The invention claimed is:
1. A method for identifying and treating a patient who is susceptible to healthcare-associated infections (HAI), comprising the steps of
obtaining a biological sample from said patient, wherein the patient is a human of at least 60 years of age who is an inpatient in a health-care facility, and wherein said biological sample is selected from the group consisting of blood, plasma and serum,
measuring the expression level of each of
high sensitivity C-reactive protein (hs-CRP) and/or interleukin-6 (IL-6),
intestinal-type fatty acid-binding protein (I-FABP), and
soluble CD14 (sCD14)
in said biological sample obtained from said patient, wherein said measuring is performed using an assay selected from the group consisting of quantitative PCR, immunoassay, biotin/avidin assay, radioimmunoassay, immunoturbidimetric assay, ELISA and electrophoretic separation, comparing said expression levels measured in said measuring step with predetermined reference levels of said hs-CRP and/or IL-6, I-FABP and sCD14,
identifying that the patient has an at least 6-fold increase in susceptibility to HAI and is thus a candidate for prophylaxis and/or treatment of nosocomial infection when expression levels of
hs-CRP and/or IL-6 is greater than or equal to predetermined reference level median,
I-FABP is greater than or equal to predetermined reference level $75^{th}$ percentile, and
sCD14 is greater than or equal to predetermined reference level median; and
administering an antibiotic to the patient identified as having said at least 6-fold increase in susceptibility to HAI.

2. The method according to claim 1, wherein the patient is at least 75 years of age.

3. The method according to claim 1, wherein the patient is an HIV-infected patient.

4. The method according to claim 1, wherein the patient is afflicted with a condition leading to immunodeficiency or is diagnosed with a co-morbidity factor.

5. The method according to claim 1, wherein the expression levels of hs-CRP, I—FABP and sCD14 are measured in said measuring step.

6. The method of claim 1, wherein expression levels of hs-CRP and/or IL-6, I-FABP and sCD14 are measured by ELISA in said measuring step.

7. The method of claim 1, wherein the healthcare facility is a geriatric rehabilitation unit.

8. A method for identifying and treating a patient who is susceptible to healthcare-associated infections (HAI) due to immunosenescence, wherein the patient is a human of at least 60 years of age who is an inpatient in a health-care facility, comprising the steps of obtaining a biological sample from said patient, wherein said blood sample is selected from the group consisting of whole blood, plasma and serum,
measuring the expression level of each of
high sensitivity C-reactive protein (hs-CRP) and/or interleukin-6 (IL-6),
intestinal-type fatty acid-binding protein (I-FABP) and soluble CD14 (sCD14)
in the blood sample obtained from said patient using an assay selected from the group consisting of quantitative PCR, immunoassay, biotin/avidin assay, radioimmunoassay, immunoturbidimetric assay, ELISA and electrophoretic separation,
comparing said expression levels measured in said measuring step with predetermined reference levels of said hs-CRP and/or IL-6, I-FABP and sCD14,
identifying that the patient has an at least 6-fold increase in susceptibility to HAI due to immunoscenescence and is thus a candidate for an anti-infective treatment and/or treatment of nosocomial infection when expression levels of
hs-CRP and/or IL-6 is greater than or equal to predetermined reference level median,
I-FABP is greater than or equal to predetermined reference level $75^{th}$ percentile, and
sCD14 is greater than or equal to the predetermined reference level median; and
identifying that the patient is susceptible-to HAI due to immunosenescence and is thus a candidate for prophylaxis and/or treatment of nosocomial infections, and
administering an antibiotic to the patient identified as having an at least 6-fold increase in susceptibility to HAI due to immunosenescence.

9. The method of claim 8, wherein the health care facility is a geriatric rehabilitation unit and the patient is at least 75 years of age.

* * * * *